US011686097B2

(12) United States Patent
Blundo et al.

(10) Patent No.: US 11,686,097 B2
(45) Date of Patent: Jun. 27, 2023

(54) SKYLIGHTS WITH INTEGRATED PHOTOVOLTAICS AND REFRACTIVE LIGHT-STEERING

(71) Applicant: Arizona Board of Regents on Behalf of Arizona State University, Scottsdale, AZ (US)

(72) Inventors: Tyler Blundo, Ringwood, NJ (US); Christiana Honsberg, Tempe, AZ (US); Stephen Goodnick, Fort McDowell, AZ (US); Richard King, Tempe, AZ (US); Nicholas Irvin, Phoenix, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 3 days.

(21) Appl. No.: 17/102,191

(22) Filed: Nov. 23, 2020

(65) Prior Publication Data

US 2021/0156151 A1 May 27, 2021

Related U.S. Application Data

(60) Provisional application No. 62/939,540, filed on Nov. 22, 2019.

(51) Int. Cl.
*E04D 13/03* (2006.01)
*F21S 11/00* (2006.01)
(Continued)

(52) U.S. Cl.
CPC .............. *E04D 13/033* (2013.01); *E06B 9/24* (2013.01); *F21S 11/002* (2013.01); *G02B 5/208* (2013.01);
(Continued)

(58) Field of Classification Search
CPC ...... E04D 13/033; F21S 11/002; H02S 20/22; H02S 20/23; H02S 20/24; H02S 20/25;
(Continued)

(56) References Cited

U.S. PATENT DOCUMENTS 6,014,845 A * 1/2000 Jain ....................... E04D 13/033
359/597
8,146,296 B2 * 4/2012 Nishikawa ........... A01G 9/1415
52/173.3
(Continued)

OTHER PUBLICATIONS

Bowden, S. et al., "Carrier Lifetime as a Developmental and Diagnostic Tool in Silicon Heterojunction Solar Cells," In 2006 IEEE 4th World Conference on Photovoltaic Energy Conference, 2006, vol. 2., pp. 1295-1298.
(Continued)

*Primary Examiner* — William V Gilbert
(74) *Attorney, Agent, or Firm* — Elliott, Ostrander & Preston, P.C.

(57) ABSTRACT

A skylight for a building includes a solar panel arranged within the skylight, the solar panel comprising one or more photovoltaic cells to collect direct radiation from rays of sunlight for conversion to electrical power, and an optical element to receive the direct radiation and refract it to the solar panel, and to receive the direct radiation and diffuse radiation scattered from the rays of sunlight and refract the direct radiation and the diffuse radiation through the skylight, bypassing the solar panel, to provide daylighting in the building.

15 Claims, 8 Drawing Sheets

(51) Int. Cl.
  *G02B 5/32* (2006.01)
  *G02B 5/20* (2006.01)
  *H02S 40/22* (2014.01)
  *E06B 9/24* (2006.01)
  *H02S 20/26* (2014.01)

(52) U.S. Cl.
  CPC .............. *G02B 5/32* (2013.01); *H02S 20/26* (2014.12); *H02S 40/22* (2014.12); *E06B 2009/2417* (2013.01); *E06B 2009/2494* (2013.01)

(58) Field of Classification Search
  CPC .. H02S 20/26; H02S 40/22; E06B 2009/2417; E06B 2009/2476; E06B 2009/2482; E06B 2009/2494; E06B 9/24; G02B 5/208; G02B 5/32; Y02B 10/10; Y02E 10/52
  USPC ................................................ 52/173.3, 200
  See application file for complete search history.

(56) References Cited

U.S. PATENT DOCUMENTS

| | | | |
|---|---|---|---|
| 8,614,842 B2 | 12/2013 | Aspnes et al. | |
| 11,290,055 B2* | 3/2022 | Wanka | F24S 23/10 |
| 2009/0014053 A1* | 1/2009 | Schulz | F24S 23/31 |
| | | | 136/246 |
| 2009/0255569 A1* | 10/2009 | Sampsell | H01L 31/022425 |
| | | | 136/246 |
| 2010/0126556 A1* | 5/2010 | Benitez | F24S 23/31 |
| | | | 136/246 |
| 2011/0116012 A1* | 5/2011 | Biernath | G02F 1/133606 |
| | | | 349/64 |
| 2011/0154749 A1* | 6/2011 | Chen | F24S 40/44 |
| | | | 52/173.3 |
| 2012/0167492 A1* | 7/2012 | Cummings | F24S 80/54 |
| | | | 52/173.3 |
| 2014/0090687 A1* | 4/2014 | Den Boer | G02B 3/0062 |
| | | | 136/246 |
| 2014/0160784 A1* | 6/2014 | Badahdah | H01L 31/0543 |
| | | | 362/558 |
| 2015/0311857 A1* | 10/2015 | Didomenico | F24S 23/00 |
| | | | 136/246 |
| 2016/0027943 A1* | 1/2016 | Bracamonte | H01L 31/0547 |
| | | | 136/246 |
| 2018/0097134 A1* | 4/2018 | Hsieh | H02S 20/21 |
| 2020/0091363 A1* | 3/2020 | Gupta | H01L 31/0547 |

OTHER PUBLICATIONS

Bowden, S. et al., "Determining lifetime in silicon blocks and wafers with accurate expressions for carrier density," Journal of Applied Physics, 2007, 102(12), pp. 124501.
Bowden, S., et al., "Application of Static Concentrators to Photovoltaic Roof Tiles," Progress in Photovoltaics: Research and Applications, vol. 3, No. 6 (Nov. 1995), pp. 413-423.
Bremner, S.P. et al., "Impact of stress relaxation in GaAsSb cladding layers on quantum dot creation in InAs/GaAsSb structures grown on GaAs (001)," Journal of Applied Physics, 2013, 114(10), p. 103511.
Castro, J.M, et al., "Energy collection efficiency of holographic planar solar concentrators," Applied Optics, vol. 49, Issue 5 (2010), pp. 858-870.
Choi, J.Y. et al., "Fabrication of Periodic Silicon Nanopillars in a Two-Dimensional Hexagonal Array with Enhanced Control on Structural Dimension and Period," Langmuir, 2015, 31(13), pp. 4018-4023.
Dahal, S. N. et al., "Identification of candidate material systems for quantum dot solar cells including the effect of strain," Progress in Photovoltaics: Research and Applications, 2010, 18(4), pp. 233-239.
Das, U. et al., "Effect of Process Parameter Variation in Deposited Emitter and Buffer Layers on the Performance of Silicon Heterojunction Solar Cells," In 2006 IEEE 4th World Conference on Photovoltaic Energy Conference, 2006, vol. 2, pp. 1283-1286.
Das, U.K. et al., "Surface passivation and heterojunction cells on Si (100) and (111) wafers using dc and rf plasma deposited Si:H thin films," Applied Physics Letters, 2008, 92(6), p. 063504.
Herasimenka, S. Y. et al., ">750 mV open circuit voltage measured on 50 μm thick silicon heterojunction solar cell," Applied Physics Letters, 2013, 103(5), p. 053511.
Jones-Albertus, R., et al., "Technology advances needed for photovoltaics to achieve widespread grid price parity," Progress in Photovoltaics: Research and Applications vol. 24, No. 9 (2016), 12 pages.
King, R. R., et al., "Effects of Temperature-Induced Bandgap Shift in 5-Junction Solar Cells," Proc. 28th European Photovoltaic Solar Energy Conf., Paris, France, Sep. 30-Oct. 4, 2013, 6 pages.
King, R.R. et al., "40% efficient metamorphic GaInP/GaInAs/Ge multijunction solar cells," Applied physics letters, 2007, 90(18), p. 183516.
King, R.R. et al., "Band gap-voltage offset and energy production in next-generation multijunction solar cells," Progress in Photovoltaics: Research and Applications, 2011, 19(7), pp. 797-812.
King, R.R. et al., "Band-Gap Engineered Architectures for High-Efficiency Multijunction Concentrator Solar Cells," 24th European Photovoltaic Solar Energy Conference and Exhibition, Hamburg, Germany, 2009. vol. 21, p. 55.
King, R. R. et al., "Solar cell generations over 40% efficiency," Progress in Photovoltaics: Research and Applications, 2012, 20(6), pp. 801-815.
Kurtz, S. et al., "Solar research not finished," Nature Photonics, 2016, vol. 10, No. 3, pp. 141-142.
Lee, J., et al., "Limiting Efficiencies of Multijuction Solar Cells With multiple Exciton Generation," IEEE Journal of Photovoltaics, 2014, 4(3), pp. 874-880.
Levy, M.Y. et al., "Absorption coefficients of intermediate-band media," Journal of Applied Physics, 2009, 106(7), p. 073103.
Levy, M.Y. et al., "Solar cell with an intermediate band of finite width," Physical Review B, 2008, 78(16), p. 165122.
Lu, M. et al., "Interdigitated back contact silicon heterojunction solar cell and the effect of front surface passivation," Applied Physics Letters, 2007, 91(6), p. 063507.
Sinton, R.A. et al., "Evaluating Silicon Blocks and Ingots with Quasi-Steady-State Lifetime Measurements," Proceedings of the 19th European Photovoltaic Solar Energy Conference, Paris, France, 2004, pp. 520-523.

* cited by examiner

SKYLIGHTS WITH INTEGRATED PHOTOVOLTAICS AND REFRACTIVE LIGHT-STEERING

CROSS-REFERENCE TO RELATED APPLICATIONS

This nonprovisional patent application claims priority to provisional patent application No. 62/939,540, filed Nov. 22, 2019, entitled "Skylights with Integrated Photovoltaics and Refractive Light-Steering", the contents of which are incorporated herein by reference.

STATEMENT OF GOVERNMENT INTEREST

This invention was made with government support under 1041895 awarded by the National Science Foundation. The government has certain rights in the invention.

TECHNICAL FIELD

The invention relates to skylights with integrated photovoltaics. Embodiments use substantially vertically positioned solar panels comprising one or more photovoltaic cells, and refractive glass, for steering direct light toward the solar panels, while allowing diffuse light to pass through the refractive glass for daylighting.

BACKGROUND

Attempts have been made to integrate photovoltaics with skylights. Typically, such attempts are based on the concept of repurposing an undesirable portion of the solar spectrum for photovoltaic energy conversion, while attempting to maintain the benefits of the skylight.

BRIEF DESCRIPTION OF THE DRAWINGS

Embodiments are illustrated by way of example, and not by way of limitation, and will be more fully understood with reference to the following detailed description when considered in connection with the figures in which.

DETAILED DESCRIPTION

Figure 1A:
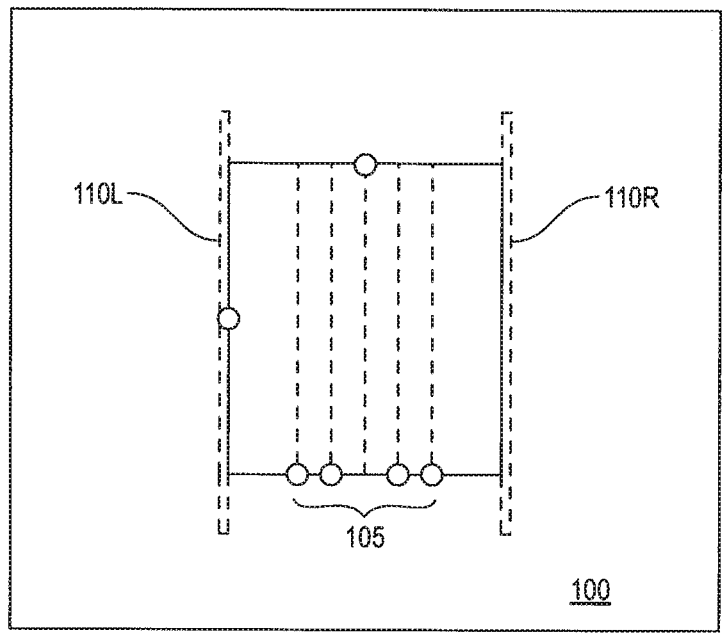
FIG. 1A is a top view of a schematic of an embodiment of the invention.

According to aspects of the embodiments of the invention, a skylight for a building, comprises a solar panel arranged within the skylight, the solar panel comprising one or more photovoltaic cells to collect direct radiation from rays of sunlight entering the skylight for conversion to electrical power and reflect diffuse radiation to provide daylighting in the building. The skylight further includes an optical element arranged within the skylight between the rays of sunlight entering the skylight and the solar panel to intercept the direct radiation and refract and/or reflect it to the solar panel, and receive the direct radiation and diffuse radiation scattered from the rays of sunlight and refract and/or reflect the direct and/or diffuse radiation through the skylight to provide daylighting in the building.

According to further aspects of the embodiments of the invention, the solar panel arranged within the skylight is arranged within the skylight to be substantially normal to a plane of a roof or wall of a building when the skylight is installed in the roof or wall of the building.

According to further aspects of the embodiments of the invention, a second solar panel is arranged within the skylight to be substantially normal to a plane of a roof or wall of a building when the skylight is installed in the roof or wall of the building. According to further aspects of the embodiments of the invention, the optical element is positioned between the first and second solar panels.

According to further aspects of the embodiments of the invention, the solar panel arranged within the skylight is arranged within the skylight to be substantially normal to a direction of the rays of sunlight when the skylight is installed in a wall or roof of the building. According to further aspects of this embodiment of the invention, the solar panel comprises a plurality of distributed photovoltaic modules with transparent spaces there between, wherein the optical element is positioned above the solar panel, substantially normal to the direction of the rays of sunlight when the skylight is installed in a wall or roof of the building, such that one or more of direct radiation and diffuse radiation is refracted through the optical element and passes through the transparent spaces to provide daylighting into the building.

According to further aspects of the embodiments of the invention, the optical element is selected from one of a group of optical elements consisting of: one or more of plurality of glass prisms; an optical film; a holographic optical element; a holographic optical element comprising a dichromated gelatin. According to further aspects of this embodiment of the invention, the optical element prevents substantially all of the direct radiation from rays of sunlight from passing through the skylight to provide daylighting in the building. According to further aspects of this embodiment of the invention, the holographic optical element comprises one or more holographic planar concentrator modules.

According to further aspects of this embodiment of the invention, the holographic planar concentrator module diffracts incident light beyond an acceptance angle of the optical element to guide light to the solar panel, wherein a concentration ratio of the holographic planar concentrator module and the acceptance angle determine the amount of light diffracted to the solar panel. According to further aspects of this embodiment of the invention, the concentration ratio of the holographic planar concentrator module and the acceptance angle that determine the amount of light diffracted to the solar panel are selected according to the amount of daylighting desired, and the amount of electrical power to be produced by the skylight.

According to further aspects of the embodiments of the invention, the solar panel arranged within the skylight comprise a solar panel arranged vertically within the skylight.

According to further aspects of the embodiments of the invention, the solar panel arranged within the skylight comprises a solar panel, having a plurality of distributed, spaced-apart photovoltaic cells, arranged horizontally within the skylight.

According to further aspects of the embodiments of the invention, the one or more photovoltaic cells comprise a plurality of emitters, wherein approximately half of the plurality of emitters facing a first side of the solar panel, and a remainder of the plurality of emitters facing a second side of the solar panel.

According to further aspects of the embodiments of the invention, the optical element reflects light from near ultraviolet and near infrared wavelengths, allowing visible portions of light to pass through the optical element.

According to further aspects of the embodiments of the invention, the optical element reflects light from near ultraviolet and near infrared wavelengths, allowing visible portions of light to pass through the optical element according to one of: the time of day; ambient building temperature; and a difference between ambient building temperature and external temperature.

In the global energy supply challenge, photovoltaic (PV) energy conversion is one part of the solution. Efficient implementation and integration with current infrastructure and technology is another part of the solution. As PV cells decrease in price and increase in efficiency, it is desirable to expand the areas in which to use them. Photovoltaic modules are useful for converting direct solar radiation into electricity, but most incident diffuse light is lost by reflection. The benefits of photovoltaics can be realized more fully by utilizing direct radiation (radiation that has not experienced scattering in the atmosphere, so that it is directionally fixed, coming from the disc of the sun) for photovoltaic energy, and selectively purposing diffuse radiation (also known as diffuse sky radiation, sky radiation, diffuse skylight, scattered radiation, and which reaches the Earth's surface after having been scattered from the direct solar beam by molecules or particulates in the atmosphere) for daylighting.

As photovoltaic cells experience steady price declines, technologies and products which increase the value of photovoltaics and which enable reduction of the levelized cost of electricity (LCOE) are of increasing interest. Photovoltaics (PV) cells integrated with other components to provide functionality beyond power generation are an important part of the next generation of modules. Such integrated PV provides a route to simultaneously increasing PV penetration, reduction in the LCOE of PV, and increase in the profitability of PV.

The goal of embodiments of the invention is a daylighting skylight with integrated photovoltaics and low cost holographic optical elements which improve performance and reduce cost compared to either a conventional photovoltaic module or a conventional daylighting skylight. These advantages include: (1) reduced cost of electricity generation; (2) lower capital expenditures for the photovoltaic module; (3) ability to tailor during which periods of the day the module captures light, even for roof slopes not facing south or southwest; (4) improved quality of lighting and energy efficiency, and the direct light component (which is generally undesirable in commercial applications) does not enter the building, rather diffuse radiation (also known as diffuse sky radiation, sky radiation, diffuse skylight, scattered radiation, and which reaches the Earth's surface after having been scattered from the direct solar beam by molecules or particulates in the atmosphere) is used for daylighting, and (5) integration into existing building products.

In addition to generating electricity, embodiments of the invention reduce the heat gain from sunlight entering the building through the skylight, thus reducing facility HVAC (Heating Cooling and Ventilation) expenditures. Embodiments also produce a more pleasant lighting effect as traditional skylights tend to introduce glare from sunlight. A prototype of an embodiment demonstrates the concept of refractive elements steering light toward vertical solar panels, as would take place within a hypothetical skylight.

Embodiments of the invention may be used in commercial daylighting applications, where many such skylights are a commonly used, deployed, for example, in an array of rows of skylights across a building's roof top. Embodiments of the invention avoid the drawbacks of building integrated photovoltaics (BIPV) while retaining BIPV advantages. BIPV is recognized as an approach to increase PV value and decrease cost by using PV to displace construction elements, e.g. a roof or window. However, existing products have a different look than existing building products, and are more suited to unique, architect-designed applications. Embodiments of the invention use an approach that is different in that the embodiments directly integrate into existing markets. The design of the PV skylight according to embodiments of the invention recognizes that under conditions of lower solar insolation (e.g., cloudy weather, morning), the amount of electricity generation is relatively small, while the need for light for daylighting is increased. Overall, the advantages of the PV skylight according to embodiments of the invention include:

1. Lower effective LCOE, since the module also acts as a construction element;
2. Reduced solar panel costs by using low concentration (2X-4X);
3. Improved performance for skylights by reducing heat gain and glare at peak sunlight time periods;
4. Reduced weight of the PV module—important for commercial roofing;
5. In many locations, good alignment with peak loads due to higher air-conditioning loads near mid-day or high solar insolation, reducing issues with integration of PV into the electrical grid;
6. Avoid a key constraint when using optical elements in photovoltaics, namely, that very thin modules dramatically reduce the flexibility in the optical design; and
7. PV integrated into construction processes that already have resources for permitting.

Relevance to Department of Energy (DOE) goals: A PV skylight according to embodiments of the invention directly addresses the DOE goals for the Photovoltaic research and development (PVRD) program, targeting an advanced module concept previously unexplored in BIPV which is rapidly deployable and enables simultaneous cost reductions in PV while realizing benefits in energy efficiency for buildings. In addition, the PV skylight according to embodiments of the invention addresses many issues which are a barrier to further deployment, including having a low cap-ex cost due to lower number of solar panels.

Embodiments of the invention provide a daylighting skylight with integrated PV which has benefits compared to both a conventional daylighting skylight and a conventional PV module. Beyond these benefits, embodiments of the invention also provide:

Immediately applicable approach to BIPV;

PV-integrated daylighting skylight which has LCOE of <$0.05/kWh;

Addresses issues such as interactions with utilities and integration of PV into the electrical grid;

Solves issues in daylighting skylights such as glare and heat gain; and

A range of optical designs which can be integrated into a daylighting skylight, the most suitable for given light or other constraints.

Daylighting is the illumination of buildings by natural light. Embodiments of the invention, using a non-imaging optical system (NIOS) in a skylight, receive direct light, or direct radiation, that is incident on, i.e., that falls on or is directed to (through refraction), one or more PV modules in the NIOS, while indirect light, or diffuse radiation, is steered through the NIOS for indoor daylighting. Embodiments improve daylighting skylights through the use of one or more photovoltaic modules and one or more low-cost optical elements. Embodiments of the invention, such as the embodiment 100 depicted in FIGS. 1A, 1B, and 1C, include dispersive glass prisms 105, e.g., a plurality of triangular-shaped glass objects.

Figure 1B:
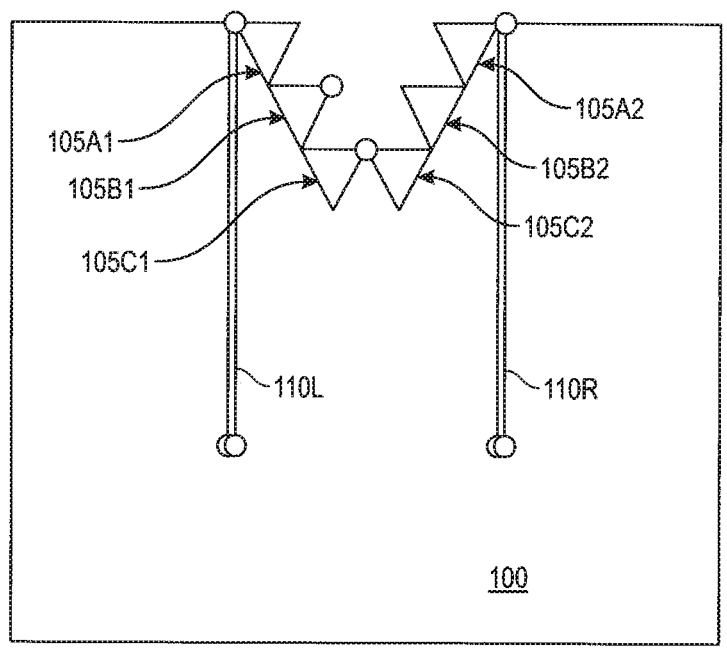
FIG. 1B is a front view of a schematic of an embodiment of the invention.

In the embodiment 100 illustrated in FIGS. 1A and 1B, triangular-shaped, for example, equilateral triangle-shaped, glass objects 105A1, 105A2, 105B1, 105B2, 105C1 and 105C2 are oriented in an inverted, or upside down, manner, with one side, a base, of the triangle-shaped glass object aligned with an exterior surface of the skylight. For example, if the skylight is installed in a horizontally oriented roof of a building, the base is aligned with a horizontally oriented exterior surface of the skylight. A first, uppermost, layer of glass prisms includes a pair of glass prisms 105A1, 105A2 positioned near the top horizontal surface of the skylight, separated and their longitudinal axes parallel, or substantially parallel, with respect to each other. The plane of the base of the glass prisms substantially aligns with the top horizontal surface of the skylight. The prisms receive direct radiation from the sun. A second, lower, layer or glass prisms includes a second pair of glass prisms 105B1, 105B2 separated and parallel with respect to each other, each positioned near or adjacent the respective pair of glass prisms 105A1, 105A2 in the first, uppermost, layer, but inset so that the bases of these prisms also receive direct radiation from the sun. In one embodiment, a vertex at the base and side of the glass prisms 105B1, 105B2, meets the lower vertex of glass prisms 105A1, 105A2, respectively. Some embodiments may include more than two layers of glass prisms, such as a third, lowermost, layer comprising glass prisms 105C1, 105C2, separated and parallel with respect to each other, each positioned adjacent the respective pair of glass prisms 105B1, 105B2 in the second layer, but inset so that a vertex at the base of the glass prisms 105C1, 105C2, meets the vertex at the top of the glass prisms 105B1, 105B2, respectively, so the third layer of prisms can receive direct radiation. In one embodiment, the layers of pairs of prisms are arranged such that no space or gap exists between the prisms in the skylight so that no direct radiation passes through any space between the layers of prisms.

In an alternative embodiment, a gap may exist between the prisms in each layer, and between layers, and an transparent, transparent-UV blocking, opaque, or semi-transparent waterproof or weatherproof cover may be installed at the top of the skylight so as to diffuse any direct radiation that would otherwise pass through space between the prisms and create glare inside the building. Similarly, or additionally, if one or more gaps exist between the prisms, an opaque or semi-transparent cover be installed at the bottom of the skylight so as to diffuse any direct radiation that would otherwise pass through space between the prisms and create glare inside the building.

The non-imaging optical elements 105A1, 105A2, 105B1, 105B2, 105C1, 105C2 (collectively, "105") are arranged in a substantially horizontal, stepped-down, parallel manner, to reflect and refract direct radiation toward one or more vertically oriented solar panels, e.g., solar panels 110L, 110R, each comprising one or more PV cells which absorb and collect the energy therefrom for conversion to electrical energy. Such embodiments of the invention reduce the heat gain associated with traditional skylight modules while improving indoor light quality, generate electricity while reducing lighting costs, thus minimizing carbon footprint and reliance on the electrical grid for power supply.

It is appreciated that the skylight may be installed in a wall or roof that is not horizontal but somewhere between vertical and horizontal, in which case, a solar panel 110L or 110R is arranged within the skylight to be substantially normal to a plane of the roof or wall of a building when the skylight is installed in the roof or wall of the building. In an alternative embodiment, solar panels 110L, 110R are arranged within the skylight at an angle other than 90 degrees with respect to the plane of the roof or wall of a building when the skylight is installed in the roof or wall of the building. For example, if the plane of the roof or wall is aligned along a first vector, and the plane of a solar panel aligned along a second vector, the angle between the first and second vector may range, for example, from 60 to 120 degrees.

Figure 3:
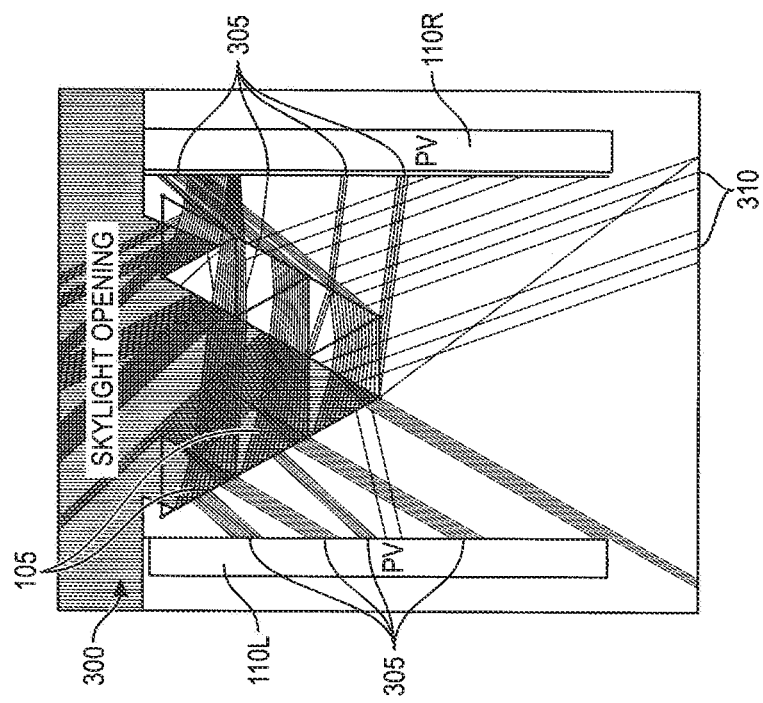
FIG. 3 is a front view of an embodiment of the invention under a sunlight-simulating lamp before or after solar noon.
Figure 2:
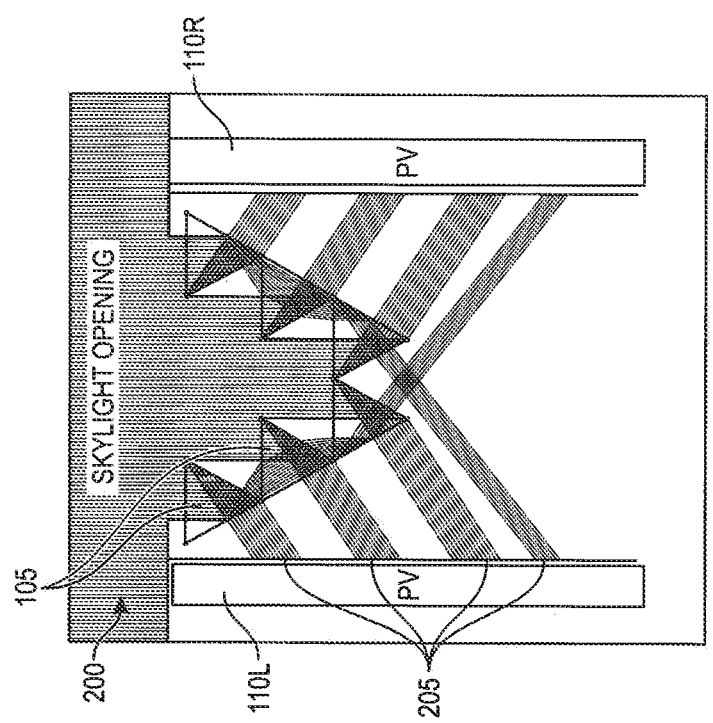
FIG. 2 is a front view of an embodiment of the invention under a sunlight-simulating lamp at solar noon.

With reference to FIGS. 2 and 3, prisms 105 in the embodiments steer direct radiation to solar panels 110, and provide diffuse radiation for daylighting in a building in which the embodiment is installed based on direct radiation that refracts through and reflects from prisms 105 and that reflects from solar panels 110. FIG. 2 illustrates direct radiation 200 entering a skylight, according to an embodiment, at solar noon—with the sun's rays directly overhead—and passing through prisms 105 which refract direct radiation toward solar panels 110, either directly from a prism or indirectly through two or more prisms, as depicted at 205. Diffuse radiation emanating from prisms 105 and reflecting off of solar panels 110L and 110R provide daylighting in the building. FIG. 3 illustrates direct radiation 300 entering a skylight, according to an embodiment, at before or after noon—with the sun's rays entering the skylight at an angle rather than straight down. Just as depicted in FIG. 2, the rays pass through prisms 105 which refract direct radiation toward solar panels 110, either directly from a prism or indirectly through two or more prisms, as depicted at 305. Diffuse radiation emanating from prisms 105 and reflecting off of solar panels 110L and 110R, and in some cases, emanating directly from prisms 105 into the building as depicted at 310, provide daylighting in the building.

Several experiments were carried out to demonstrate the functionality of embodiments of the invention illustrated in FIGS. 1A, 1B, 2 and 3. These experiments show that the embodiments result in an eighty-four percent reduction in heat gain, compared to a typical skylight. The desired light steering and daylighting effect was also demonstrated.

Embodiments of the invention involve skylights with integrated photovoltaics (PV). According to the embodiments, one or more vertical solar panels 110L, 110R, each comprising one or more photovoltaic cells, and one or more refractive glass elements (e.g., 105A1, 105A2, 105B1, 105B2, 105C1, 105C2) for steering direct light toward the solar panels, capture direct radiation or light, while allowing diffuse radiation or light to pass through the refractive glass elements of the skylight.

According to one embodiment, one or more solar panels are placed vertically within a skylight. The solar panels are oriented vertically, or substantially vertically, and positioned separate from one another, in order to avoid blocking direct sunlight. The PV cells on each panel have their emitters facing toward the optical elements to receive direct light refracted and reflected from the optical elements.

Figure 1C:
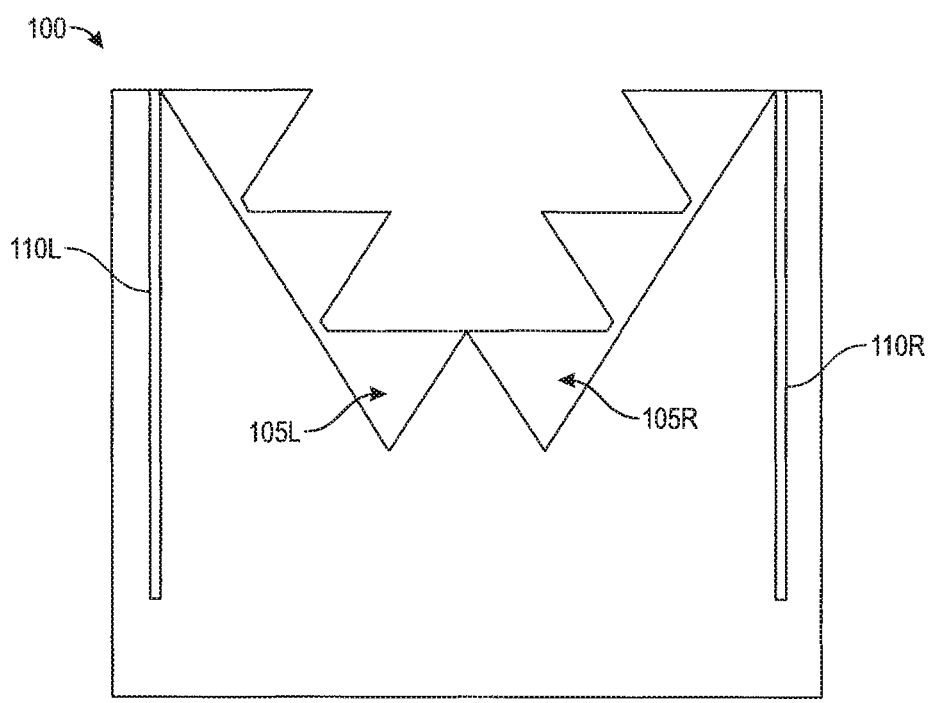
FIG. 1C is a front view of a schematic of an embodiment of the invention.

According to one embodiment, the refractive glass elements 105 are suspended within the skylight, as depicted in FIG. 1B. This refractive glass bends the direct light toward the solar panels 110 for collection. The refractive glass may be in the form of long equilateral triangular prisms, as used in the embodiment, but glass with curved edges may also be used. The refractive glass also prevents most direct sunlight from entering the building. This embodiment may allow some direct sunlight into a building in which the skylight is installed. FIG. 1C illustrates another embodiment, in which a single refractive glass element 105L or 105R in the shape of a sawtooth is used, and which operates in the same or similar manner as the embodiment disclosed in FIG. 1B.

Figure 4:
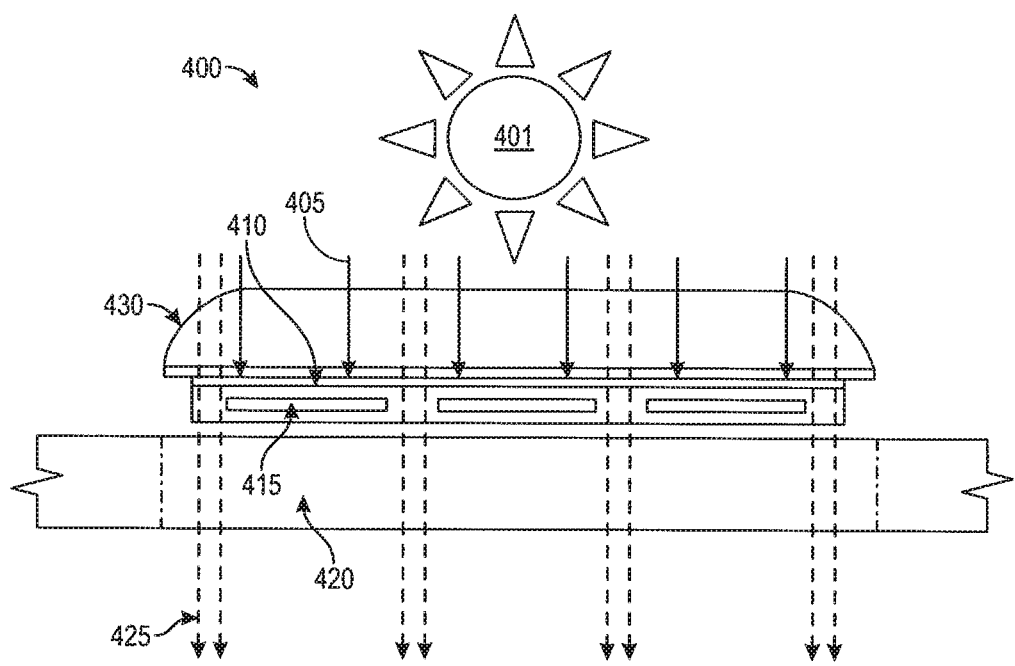
FIG. 4 depicts one embodiment comprising solar panels in a transparent skylight, containing low-cost light steering optics.

Another embodiment of the invention involves a PV module with integrated daylighting, enabling both electricity production and decreased energy usage. This embodiment 400 comprises a solar panel with one or more solar cells 415 in a transparent or semi-transparent skylight situated on a roof 420, containing low-cost light steering optics, for example, in optical film 410, as shown in FIG. 4. In this embodiment 400, direct radiation 405 is received during several hours of the day when the sun 401 is directly overhead and is directed through clear or opaque waterproof or weatherproof cover 430, towards the solar panel comprising PV cells 415. Diffuse radiation 425 that does not hit the solar panels, passes through, between the solar panels, and is used for daylighting in the building below. In one embodiment, the solar panels operate under low concentration.

Low concentration PV are systems with a solar concentration of 2-100 suns. For economic reasons, conventional or modified silicon solar cells are typically used. The heat flux is typically low enough that the cells do not need to be actively cooled. Low-concentration systems often have a simple booster reflector, which can increase solar electric output compared to non-concentrator PV systems.

Important issues for feasibility of a daylighting PV module according to embodiments of the invention are: (1) the cost/benefit of a PV skylight, not only in electricity generated, but also in improving daylighting performance; (2) the feasibility of integration of PV into the skylight, including encapsulation and mounting structures within the module; (3) the optical design and approaches, including their cost and performance. Each of these is briefly addressed below.

Figure 5:
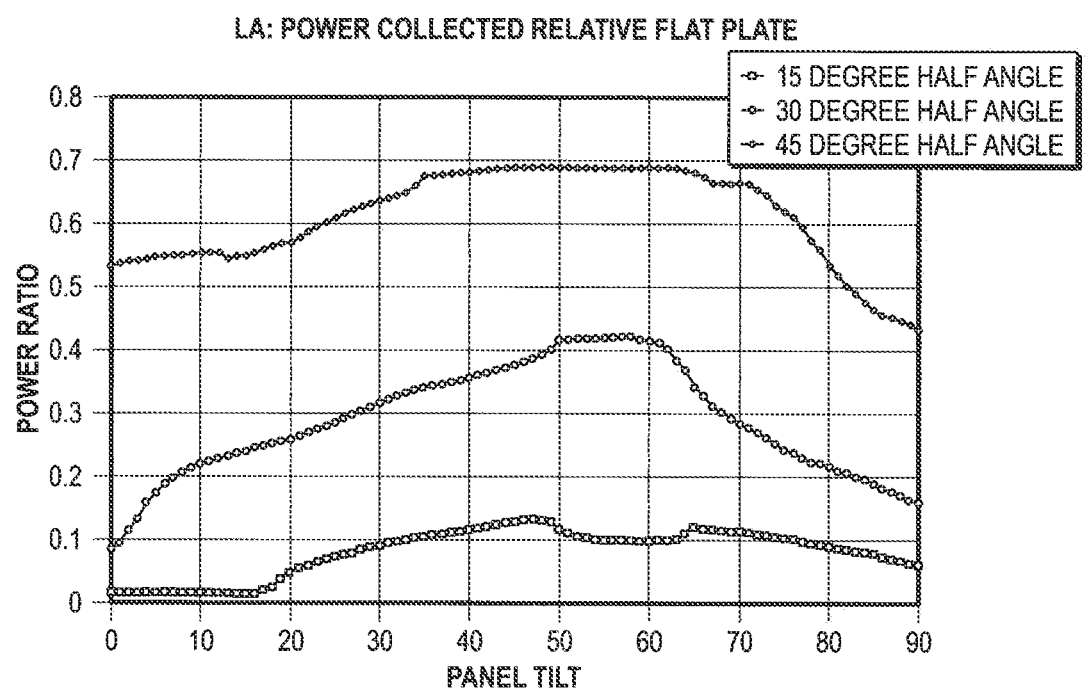
FIG. 5 graphically illustrates the ratio of power produced from a limited acceptance angle concentrator compared to peak power output.

To find LCOE: (i) calculate the incremental cost of adding PV to a skylight; (ii) estimate the added costs to the skylight; (iii) determine the electricity produced as a function of concentration and acceptance angle; (iv) calculate LCOE. The concentration is 2× to 4× depending on the acceptance angle. The calculation uses a PV cell cost of $0.5/$W_p$ to reflect the value of higher efficiency PV cells for such applications. The optics cost is $3/m². The soft costs, inverter costs, etc., use numbers consistent with R. Jones-Albertus, D. Feldman, R. Fu, K. Horowitz, and M. Woodhouse, "Technology advances needed for photovoltaics to achieve widespread grid price parity," Progress in photovoltaics: research and applications, vol. 24, no. 9, pp. 1272-1283, 2016, the entire contents of which are incorporated herein by reference. The fraction of installation costs attributable to the PV modules are the subject of new methodologies for evaluating value of PV-integrated products described in Task 2; here permitting and wiring costs are included. The electricity produced is determined by calculations as described in S. Bowden, S. R. Wenham, and M. A. Green, "Application of Static Concentrators to Photovoltaic Roof Tiles," *Prog. Photovolt: Res. Appl.*, vol. 3, no. 6, pp. 413-423, November 1995, the entire contents of which are incorporated herein by reference, where the direct and diffuse radiation as a function of acceptance angle over a year for a location is calculated and compared to flat plate PV. The results are shown in FIG. 5. The LCOE is calculated by an economic model similar to a Social Accounting Matrix (SAM) that represents flows of all economic transactions that take place, but allows modification of PV generation to account for limited acceptance angle.

Figure 6:
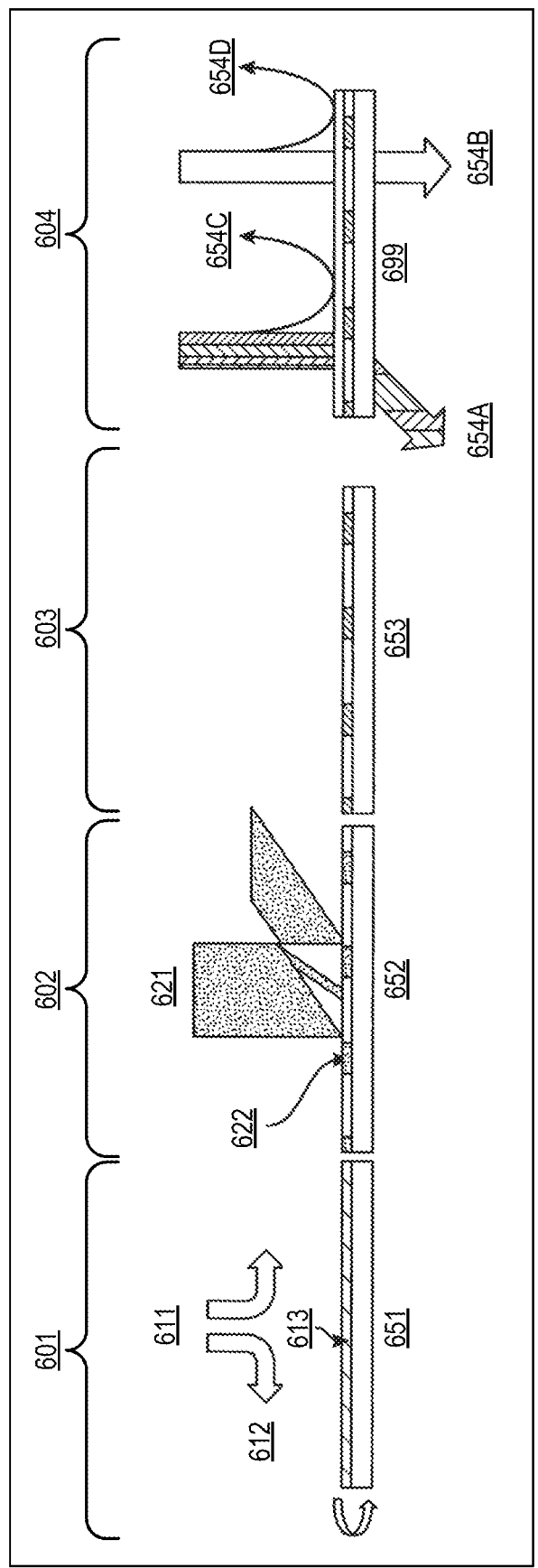
FIG. 6 illustrates a process for fabricating dichromated gelatin films.

Embodiments of the invention comprise a holographic planar concentrator module such as described in J. M. Castro, D. Zhang, B. Myer, and R. K. Kostuk, "Energy collection efficiency of holographic planar solar concentrators," Appl. Opt., Vol. 49, 858-870 (2010). An example of a commercial module is shown in FIG. 6. In particular, FIG. 6 depicts SUBSTRATE FABRICATION in the leftmost block at element 601 to provide a SOIN coating substrate 651. As shown by element 601, the substrate fabrication includes airflow at 50-degrees Celsius as indicated by element 611 using 75-200 rpm as indicated by element 612 which determines thickness of the substrate 651 using a sensitized gelatin solution 613 atop the substrate 651. Substrate fabrication 601 is followed by IMAGING in the second to left block at element 602 using coherent exposure for the substrate 652. As shown by element 602, the coherent exposure includes use of coherent waves as indicated by element 621 to yield the interference pattern 622 on the substrate 652. Imaging 602 is followed by DEVELOPMENT in the second to right block at element 603 in which soft layers encourage chirping and high order harmonics for the substrate 653, which includes the use of (1) a rapid fixer with hardener, (2) a rinse in DI water, and (3) isopropanol dehydration via (3.1) a 50% IPA, 50% DI water mix, (3.2) a 75% IPA, 25% DI water mix, and (3.3) 99.9% IPA. Lastly, development at 603 is followed by ENCAPSULATION AND RECONSTRUCTION at the rightmost block at element 604 yielding a substrate 699 with detraction in the central wavelength as indicated by element 654A and with the substrate 699 being transparent to other wavelengths as indicated by element 654B. Reflection losses are depicted by elements 654C and 654D for the substrate 699. One embodiment uses a roll-to-roll technique for fabricating large areas of holographic optical elements as per G. Rosenberg, U.S. Pat. No. 8,614,842 B2, issued 24 Dec. 2013. The holographic planar concentrator modules have passed certification for 25 years of operation without significant degradation from accelerated life testing. This same concept will be examined in work balance daylighting, heat rejection, and PV electricity production.

Embodiments of the invention provide for the integration of low cost optics, high efficiency solar panels and commercial daylighting systems to most effectively utilize solar radiation; under high insolation conditions (i.e., under high amounts of electromagnetic energy (solar radiation) incident on the surface of the earth), electricity generation is performed, and under low insolation, daylighting is emphasized. The PV skylight according to embodiments has lower LCOE that conventional PV, higher performance than conventional skylights, and circumvents typical constraints in both integrating optics into PV modules and in BIPV. In addition, since a PV skylight according to embodiments is not sensitive to PV cells costs, it provides new routes for introduction of higher efficiency concepts, increasing differentiation among manufacturers, and providing a route to innovation in photovoltaics.

A description of the design and prototype of holographic optical elements as may be utilized in embodiments of the invention, follows.

Figure 7:
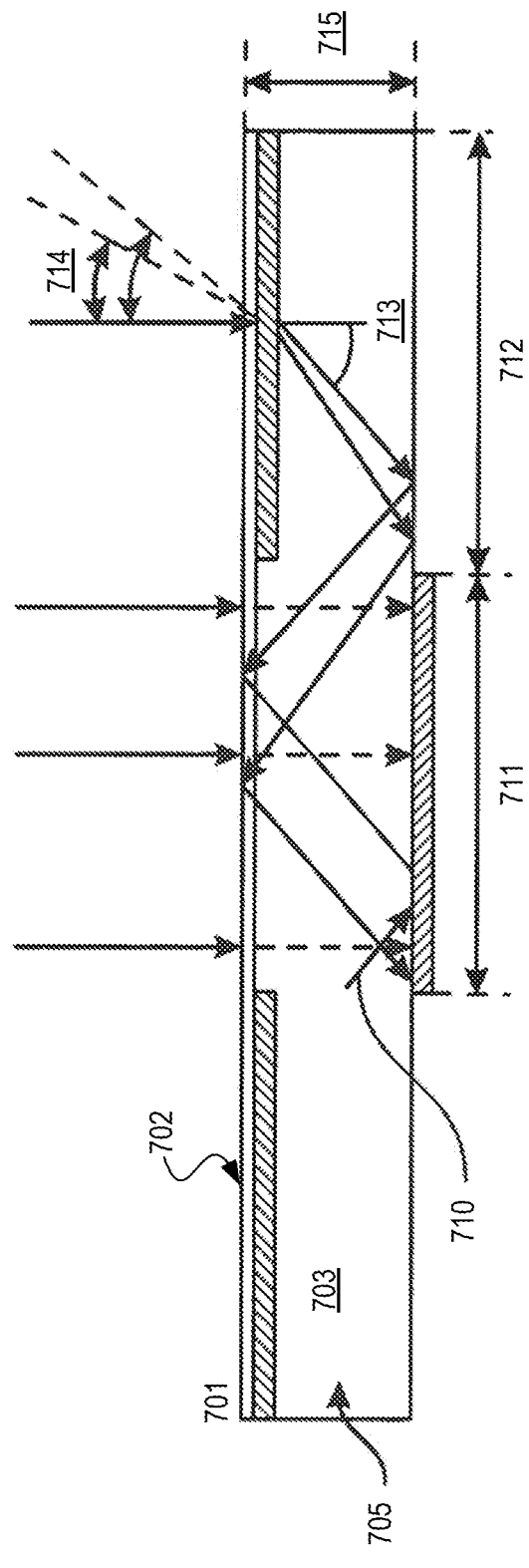
FIG. 7 is a diagram showing the operation of a holographic planar concentrator, in which the holographic optical elements diffract light beyond the critical angle of the substrate to a region where the PV cells are located.

As for the design of a holographic optical concentrator, one approach uses the technique shown in FIG. 7. The material can be used to form either a transmission or reflection type holographic optical elements that can be used in hybrid daylighting-PV applications, according to embodiments of the invention.

One embodiment implements a planar holographic concentrator 700 as shown in FIG. 7. The holographic optical elements diffract incident light beyond the critical angle of the glass substrate 705 which guides the light to the PV cells 710. The concentration ratio and acceptance angle determine the amount of light transmitted. For a higher concentration ratio (e.g., 4X), the acceptance angle is lower, limited to a half-angle acceptance of 14°, while, for example, at 2X, the half-angle is 46°. The optimum value depends on the amount of daylight desired, and the amount of power to be produced by the module. Further depicted at the planar holographic concentrator 700 is a cover glass 701 with refractive indices of $N_2$ at element 703 and $N_1$ at element 702 formed atop the glass substrate 705. The PV cell 710 is further depicted as are each of $D_{PVC}$ at element 711, dimension $D_H$ at element 712, value $\theta_{DIFF}$ at element 713, value $\theta_{INC}$ at element 714, and the dimension D at element 715.

Embodiments of the invention contemplate holographic optical elements that diffract 300-400 nm of the incident solar spectrum beyond the critical angle of a glass substrate. The diffraction may occur for at least two hours during the course of the day, according to one embodiment, depending on the position of the embodiment with respect to the direction of the sun's rays.

In addition, embodiments of the invention corresponding to FIG. 7 or variations thereof may also be used in which the cross hatched features on the upper surface of the transparent region are also photovoltaic (PV) solar cells. Such an embodiment uses strong overhead sunlight mostly for generating electricity from the photovoltaic (PV) solar cells, while diffuse light and direct sunlight at steep angles (early and late in the day) have more of their energy deflected downward for indoor lighting. The dimensions $D_H$ and D in the embodiment illustrated in FIG. 7 may be varied to increase or decrease this effect.

In this embodiment, the rays of light going through one of the solar cells on the upper surface are absent. Incident rays of sunlight at an angle theta$_{INC}$ in the gap between solar cells on the upper surface are 1) transmitted through the gap between solar cells on the upper and lower surfaces of the transparent region 705 into indoor space beneath the skylight; and 2) reflected off the top surface of the solar cell 710 on the bottom of the transparent region 705, and then reflected again off the bottom surface of a solar cell on the upper surface of the transparent region 705, so that light is again deflected toward the indoor space beneath the skylight. The solar cells may be angled, or the interface between the regions with refractive index N1 and N2 may be frosted, textured or angled, or the front surface of the cover glass may be frosted, textured, or angled to deflect more light at a steep angle with respect to normal incidence, in order to deflect more light to the indoor space beneath.

In one embodiment, the top (skyward facing) surface of the solar cells on the lower surface of the transparent region in FIG. 7 may be untextured to enhance deflection of light for indoor lighting. In another embodiment this surface of the cells is textured to increase PV cell electrical output.

In another embodiment, the solar cells on the upper surface of the transparent region in FIG. 7 are bifacial solar cells, that is, they are able to generate electricity from light that is incident on either the top or bottom surface of these cells. Further, the bottom surface (facing the indoor space) of these solar cells on the upper surface of the transparent region may: 1) be untextured to enhance deflection of light for indoor lighting; 2) be textured to increase PV cell electrical output; or 3) be fully or partially metallized with a specularly or diffusely reflective metal surface to control the amount of light deflected to indoor lighting or absorbed by the cell to increase PV electrical output.

Models of embodiments of the invention were simulated using the open-source software Ray Optics Simulation available on github.com. Based on theoretical results from the simulation, a prototype was constructed, and several experiments were carried out to demonstrate the functionality of the design. These experiments suggest that embodiments result in an eighty-four percent reduction in heat gain, compared to a typical skylight. In good agreement with the ray tracing simulations, experiments were able to reproduce the desired light steering and daylighting effect.

A skylight prototype was designed according to embodiments of the invention depicted in FIGS. 1A and 1B. Light steering capabilities of the skylight design were simulated, and a plan created to prototype and implement a small-scale version of the skylight. Then a fully functional prototype was created. The structure was built using black plexi-glass, cut using 3D print and laser cutting equipment. Diffused junction silicon solar panels were fabricated and laminated. Refractive glass prisms were purchased and mounted within clear plexi-glass below the skylight opening. Plexi-glass as referred to herein is a trade name for poly(methyl methacrylate), also known as acrylic, or acrylic glass, as well as by the trade names Crylux, Plexiglas acrylic, Acrylite, Astariglas, Lucite, Perclax, and Perspex, among several others, and is a transparent thermoplastic often used in sheet form as a lightweight or shatter-resistant alternative to glass.

Using the skylight prototype, a number of experiments were performed. These experiments include the optimization of solar cell geometry and placement, the demonstration of light steering functionality, and the demonstration of heat gain reduction. These results are presented in the following discussion.

The experimental results are compared to the simulation and their significance to the design specification are expressed. Two experiments were performed in effort to demonstrate the efficacy of the refractive prism array concept.

Figure 8:
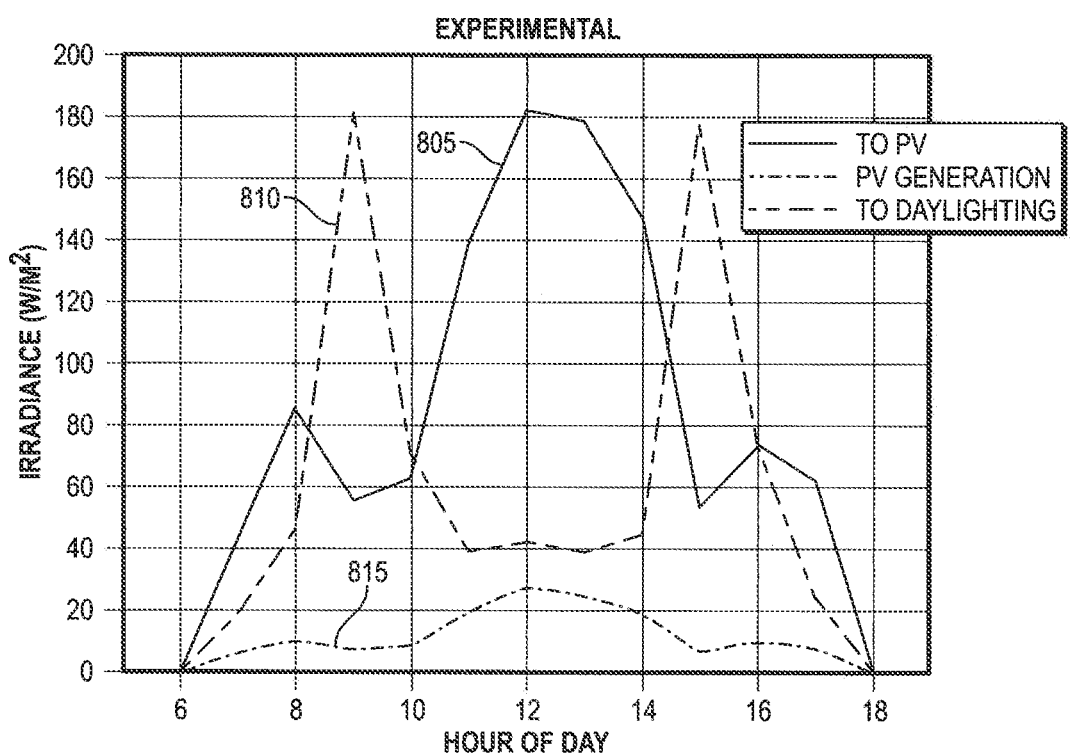
FIG. 8 is a plot of the solar irradiance available for absorption by the PV modules in accordance with an embodiment of the invention.

In the first of two experiments, the skylight prototype was used to measure the light steering properties of the refractive prism array. Using an outdoor PV tester, measurements of the skylight's PV cells were taken at each hour of the day. In order to ensure measurement accuracy, the front opening of the skylight was covered with a black tarp while taking measurements. At each hour, irradiance incident on the vertical PV cells was measured and derived from short-circuit current. This data is shown as the curve 805 in FIG. 8. Similarly, irradiance incident on the azimuth facing photodetector was measured and derived from short-circuit current. This data is shown as the curve 810 in FIG. 8 and represents light passed through for daylighting. Strong agreement was seen between the simulated results and the experimental results of FIG. 8. Additionally, the dotted curve 815 represents the output power density at each hour from the vertical PV cells.

The second experiment was a measure of the effect that the optical elements and PV cells had on heat gain within the prototype enclosure. This experiment involved the use of a Static IV Curve Tester, which is effectively a large lamp which simulates the radiation of one sun, i.e., 1000 Watts per meter squared of full spectrum irradiance.

Figure 9:
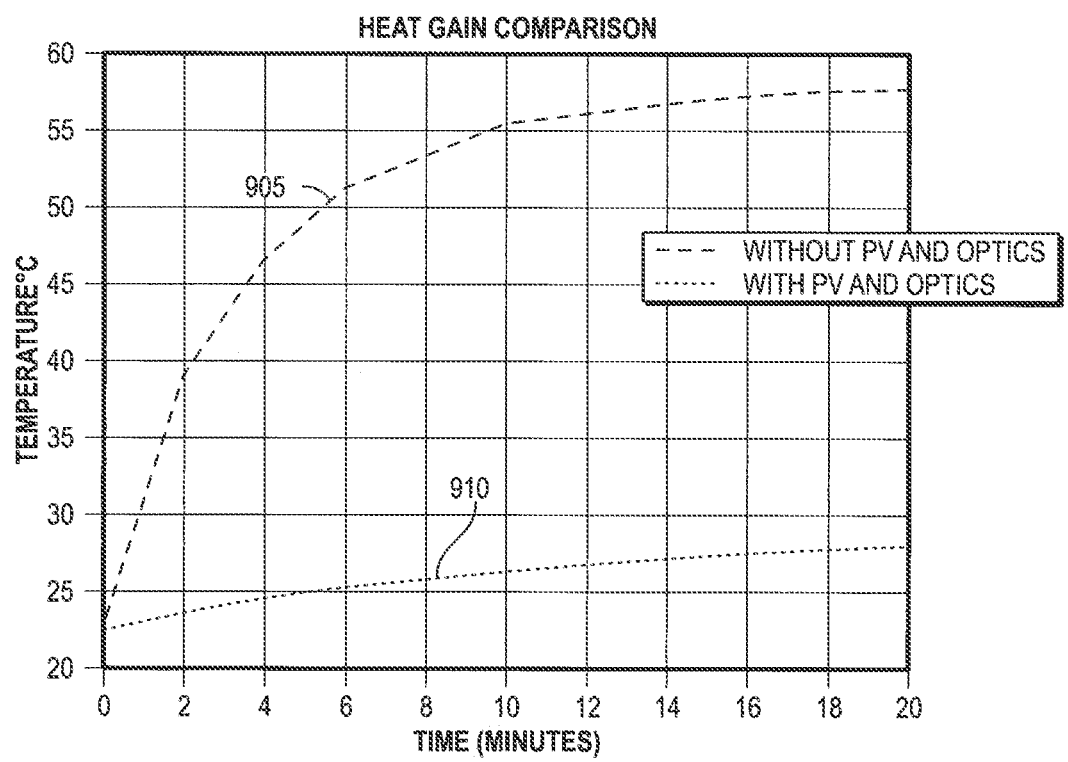
FIG. 9 is a plot showing a reduction in heat gain within a skylight in accordance with embodiments of the invention.

During this experiment, the skylight prototype was placed under the static IV tester for twenty minutes without the vertical PV cells and optical elements. Collecting data with a thermocouple in this first condition, the curve 905 in FIG. 9 was obtained. The skylight was allowed to return to room temperature. Then the same test was performed, but in this case the prototype was placed under the static IV tester for twenty minutes with the vertical PV cells and optical elements. Collecting data with a thermocouple in this second condition, the curve 910 in FIG. 9 was obtained. The curves were produced with the static IV tester lamp normal to the skylight aperture. Therefore, these results are only indicative of hours near solar noon.

The percent difference between the two curves show an 84% reduction in heat gain near solar noon. This experiment demonstrates that the design has successfully been shown to reduce heat gain entering the enclosure, and with thus contribute to a reduction in HVAC load on the facility.

The above specification and examples provide a complete description of the structure and use of exemplary embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the present devices, systems, and methods are not intended to be limited to the particular forms disclosed. Rather, they include all modifications and alternatives falling within the scope of the claims that follow, and embodiments other than the one shown may include some or all of the features of the depicted embodiment. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

What is claimed is:

1. A skylight for a building, comprising:
a solar panel arranged within the skylight, the solar panel comprising one or more photovoltaic cells to collect direct radiation from rays of sunlight entering the skylight for conversion to electrical power and reflect diffuse radiation to provide daylighting in the building; and
an optical element arranged within the skylight between the rays of sunlight entering the skylight and the solar panel, wherein the optical element is formed from multiple equilateral triangular glass objects, each oriented with one side aligned with an exterior surface of the skylight; and
wherein the solar panel is configured to:
intercept the direct radiation and refract and/or reflect it to the solar panel, and receive the direct radiation and diffuse radiation scattered from the rays of sunlight and refract and/or reflect the direct and/or diffuse radiation through the skylight to provide daylighting in the building.

2. The skylight of claim 1, wherein the solar panel arranged within the skylight is arranged within the skylight to be substantially normal to a plane of a roof or wall of a building when the skylight is installed in the roof or wall of the building.

3. The skylight of claim 2, further comprising a second solar panel arranged within the skylight to be substantially normal to a plane of a roof or wall of a building when the skylight is installed in the roof or wall of the building.

4. The skylight of claim 3, wherein the optical element is positioned between the first and second solar panels.

5. The skylight of claim 2:
wherein the solar panel arranged within the skylight is arranged parallel to the wall of the building when the skylight is installed into the wall of the building.

6. The skylight of claim 2:
wherein the solar panel arranged within the skylight comprises a solar panel, having a plurality of distributed, spaced-apart photovoltaic cells; and
wherein the solar panel arranged within the skylight is arranged parallel with the roof of the building when the skylight is installed into the roof of the building.

7. The skylight of claim 1, wherein the solar panel within the skylight is arranged to be substantially normal to a plane of a roof or wall of a building when the skylight is installed in the roof or wall of the building.

8. The skylight of claim 7, wherein the solar panel arranged within the skylight further includes a plurality of distributed photovoltaic modules with transparent spaces there between, wherein the optical element arranged within the skylight is positioned above the solar panel, substantially normal to the direction of the rays of sunlight when the skylight is installed in a wall or roof of the building, such that one or more of direct radiation and diffuse radiation is refracted through the optical element and passes through the transparent spaces to provide daylighting into the building.

9. The skylight of claim 1, wherein the optical element is selected from one of a group of optical elements consisting of:
one or more of plurality of glass prisms;
an optical film;
a holographic optical element; and
a holographic optical element comprising a dichromated gelatin.

10. The skylight of claim 9, wherein the optical element prevents a portion of the direct radiation from rays of sunlight from passing through the skylight to provide daylighting in the building.

11. The skylight of claim 9:
wherein the optical element is the holographic element; and
wherein the holographic optical element comprises one or more holographic planar concentrator modules.

12. The skylight of claim 11, wherein the holographic planar concentrator module is selectively positionable at an angle affecting an amount of incident light diffracted onto the solar panel.

13. The skylight of claim 12:
wherein the holographic planar concentrator module is configurable to diffract incident light passing the optical element to selectively guide light to the solar panel affecting an amount of daylight passing through the skylight and an amount of electrical power produced by the skylight from the daylight.

14. The skylight of claim 1, wherein the optical element reflects light from near ultraviolet and near infrared wavelengths, allowing visible portions of light to pass through the optical element.

15. The skylight of claim 14, wherein the optical element reflects light from near ultraviolet and near infrared wavelengths, allowing visible portions of light to pass through the optical element according to one of:
the time of day;
ambient building temperature; and
a difference between ambient building temperature and external temperature.

* * * * *